（12） United States Patent
Huang et al.

(10) Patent No.:     US 9,399,624 B2
(45) Date of Patent:     Jul. 26, 2016

(54) PROCESS FOR PREPARING (1S)-1-PHENYL-3,4-DIHYDRO-2(1H)-ISOQUINOLINE-CARBOXYLATE

(71) Applicants: Shanghai Jingxin Biomedical Co., Ltd., Shanghai (CN); Shangyu Jingxin Pharmaceutical Co., Ltd., Shangyu, Zhejiang (CN)

(72) Inventors: Yue Huang, Shanghai (CN); Fei Zheng, Shanghai (CN)

(73) Assignees: Shanghai Jingxin Biomedical Co., Ltd., Shanghai (CN); Shangyu Jingxin Pharmaceutical Co., Ltd., Shangyu (CN)

(*) Notice: Subject to any disclaimer, the term of this patent is extended or adjusted under 35 U.S.C. 154(b) by 0 days.

(21) Appl. No.: 14/690,282

(22) Filed: Apr. 17, 2015

(65) Prior Publication Data

US 2015/0225348 A1     Aug. 13, 2015

Related U.S. Application Data

(63) Continuation of application No. PCT/CN2013/000067, filed on Jan. 21, 2013.

(30) Foreign Application Priority Data

Oct. 30, 2012     (CN) .......................... 2012 1 0425678

(51) Int. Cl.
    C07D 217/06     (2006.01)
    C07D 453/02     (2006.01)

(52) U.S. Cl.
    CPC ............ *C07D 217/06* (2013.01); *C07D 453/02* (2013.01)

(58) Field of Classification Search
    None
    See application file for complete search history.

(56) References Cited

U.S. PATENT DOCUMENTS

| | | | |
|---|---|---|---|
| 6,017,927 | A | 1/2000 | Takeuchi et al. |
| 6,566,533 | B1 | 5/2003 | Barth et al. |
| 2002/0120140 | A1 | 8/2002 | Lee |
| 2008/0242697 | A1 | 10/2008 | Puig Serrano et al. |
| 2010/0029944 | A1 | 2/2010 | Puig et al. |

FOREIGN PATENT DOCUMENTS

| | | |
|---|---|---|
| CN | 1300730 C | 6/2001 |
| EP | 0801067 A1 | 10/1997 |
| WO | WO 2005075474 A1 | 8/2005 |
| WO | WO 2005105795 A1 | 11/2005 |
| WO | WO 2007076116 A2 | 7/2007 |
| WO | WO 2008011462 A2 | 1/2008 |
| WO | WO 2008019055 A2 | 2/2008 |
| WO | WO 2010103529 A1 | 9/2010 |

OTHER PUBLICATIONS

Mealy, N. et al., Treatment of Urinary Incontinence, Muscarinic $M_3$ Antagonist. Drugs of the Future, vol. 24 (8), pp. 871-874 (Aug. 1999).
Niphade, N.C. et al., Efficient and Single Pot Process for the Preparation of Enantiomerically Pure Solifenacin Succinate, an Antimuscarinic Agent. Monatsh, Chem. vol. 142, pp. 1181-1186 (Aug. 2011).
Peterson, S.L. et al., Parallel Synthesis of Ureas and Carbamates from Amines and $CO_2$ under Mild Conditions. Organic Letters. Internet date of publication: Feb. 22, 2010, vol. 12, No. 6, pp. 1340-1343, see table 4.
Butcher, K.J.; Carbamate Esters; A Simple, Mild Method of Formation. Synlett. Oct. 1994, No. 10, pp. 825-826, see tables 1 and 2, and the part of experiments.
Chaturvedi, D. et al., Versatile Use of Carbon Dioxide in the Synthesis of Carbamates, Monatshefte Fur Chemie. Internet date of publication: Jan. 20, 2006, vol. 137, pp. 127-145, see reaction formulae 21, 29, and 31.
Salvatore, R.N. et al., Efficient $Cs_2CO_3$-Promoted Solution and Solid Phase Synthesis of Carbonates and Carbamates in the Presence of TBAI. Tetrahedron. Apr. 22, 2002, vol. 58, No. 17, pp. 3329-3347, see reaction formulae 3-8, and tables 5-8.
Kong, D.L. et al., Polyethylene Glycol-Enhanced Chemoselevtive Synthesis of Organic Carbamates from Amines, $CO_2$, and Alkyl Halides. Synthetic Communications. Internet date of publication: Jul. 26, 2011, vol. 41, No. 22, pp. 3298-3307, see tables 1-4, and the part of experiments.
Li, Liqiang et al., One-Pot Synthesis of Carbamates, Chinese Journal of Organic Chemistry, 2007, vol. 27, No. 4, pp. 519-523, see the part of experiments.

*Primary Examiner* — Zinna Northington Davis
(74) *Attorney, Agent, or Firm* — Mei & Mark LLP; Manni Li

(57) ABSTRACT

A process for preparation of (1S)-1-phenyl-3,4-dihydro-2 (1H)-isoquinoline-carboxylate (Formula I), comprising reacting (1S)-1-phenyl-3,4-dihydro-2(1H)isoquinoline (Formula II) with carbon dioxide and an alkylating agent R-LG in the presence of a base to obtain the compound of Formula I in an organic solvent.

In Formula I and II, R is an alkyl or a substituted alkyl; LG is a leaving group.

16 Claims, No Drawings

PROCESS FOR PREPARING (1S)-1-PHENYL-3,4-DIHYDRO-2(1H)-ISOQUINOLINE-CARBOXYLATE

CROSS-REFERENCE TO RELATED APPLICATIONS

The subject application is a continuation of PCT international application PCT/CN2013/000067 filed on Jan. 21, 2013, which in turn claims priority on Chinese patent application CN201210425678.5 filed on Oct. 30, 2012. The contents and subject matter of the PCT and Chinese priority applications are incorporated herein by reference.

FIELD OF INVENTION

The present invention relates to a process for preparing a drug compound, specifically for preparing a drug intermediate, and more particularly, (1S)-1-phenyl-3,4-dihydro-2(1H)-isoquinoline-carboxylate, which is the key intermediate for preparing Solifenacin to be used as a muscarine M3 receptor antagonist for treating overactive bladder contraction.

BACKGROUND OF THE INVENTION

Solifenacin, chemically known as (3R)-1-azobicyclo[2.2.2]oct-3-yl-(1S)-1-phenyl-3,4-dihydroquionline-2-(1H)-carboxylate, and its pharmaceutically acceptable salts have highly selective antagonism to muscarine M3 receptor and are used for preventing and treating urinary diseases, such as neurogenic urinary frequency, neurogenic bladder, nycturia, unstable bladder, bladder spasm, and chronic cystitis, and respiratory diseases, such as chronic obstructive pulmonary disease, chronic bronchitis, asthma, and rhinitis. The chemical structure of Solifenacin (Cas No. [242478-37-1]) is as follows:

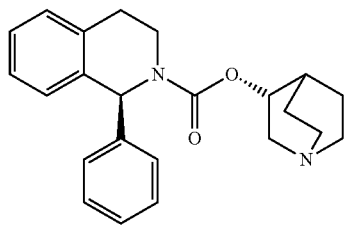

The process for preparing Solifenacin has been known, where the key step is connecting the isoquilinline moiety to the quinucilidinyl moiety via a carbonyl group

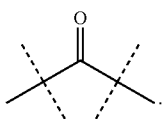

Major processes to obtain Solifenacin are as follows:

(1) Process where a triphosgene or phosgene is used:

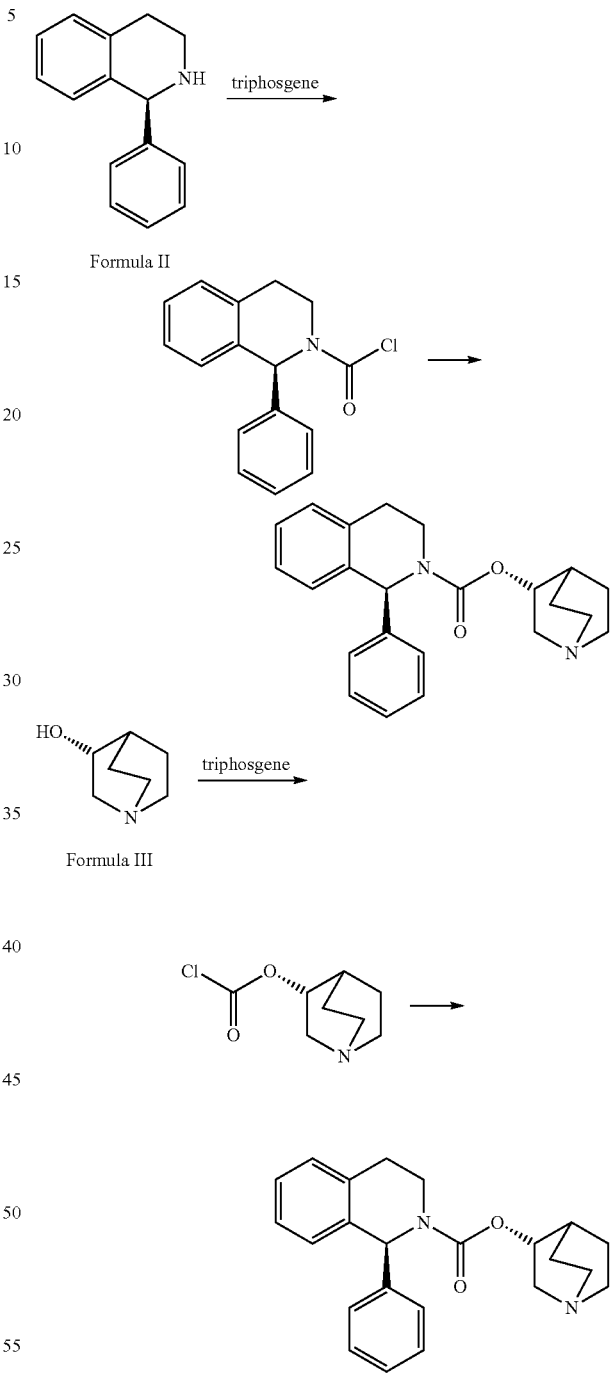

According to processes disclosed in U.S. Pat. No. 6,017,927, EP0801067, and WO2005105795, triphosgene is used to introduce the carbonyl group to synthesize Solifenacin in the presence of strong base. For the reason that the highly toxic phosgene will be inevitably released in the process, extremely high requirements on environment safety are needed. At the same time, it is hard to control the impurities, in particularly, to prevent the generation of the impurity, bis((S)-1-phenyl-3,4-dihydroisoquinolin-2(1H)-yl)methanone.

(2). Process where chloroformate used

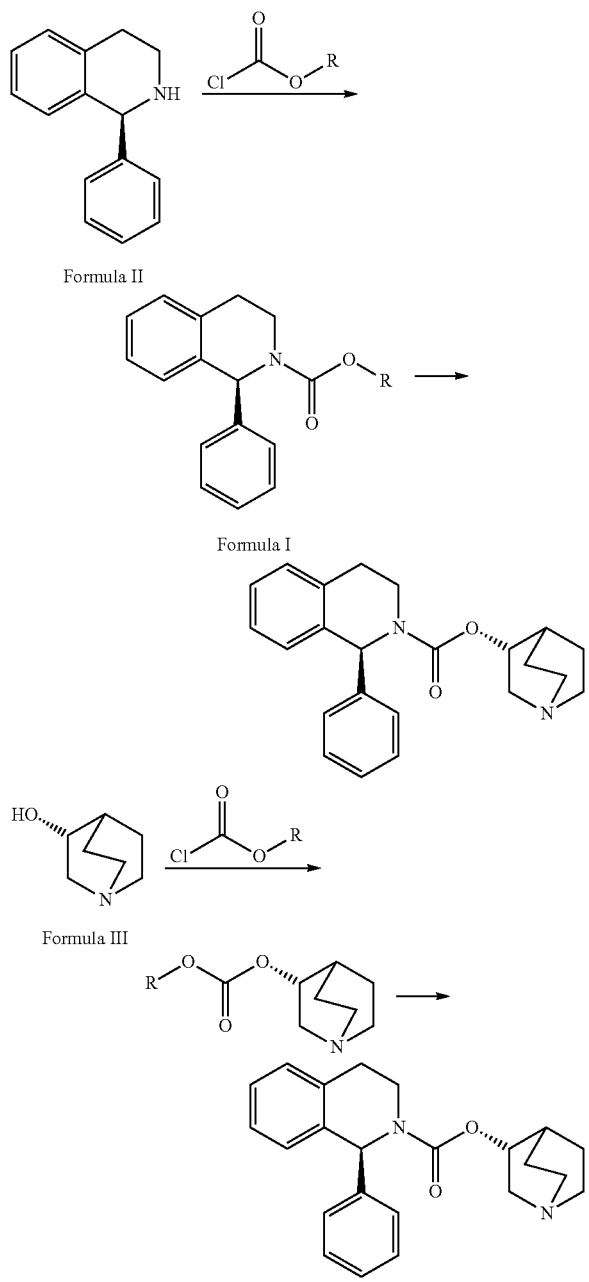

Formula II

Formula I

Formula III

R is an alkyl or a substituted alkyl. According to processes for preparing Solifenacin as disclosed in Drugs of the future 24(8), 871-874, 1999, WO2005075474, WO2007076116, WO2008011462, and WO2008019055, chloroformates are used in the process. Even though the process prevents the generation of bis((S)-1-phenyl-3,4-dihydroisoquinolin-2 (1H)-yl) methanone, the use of highly toxic chloroformates to prepare carboxylate derivatives (formula I) may cause much trouble in operation safety and environmental health.

(3). Other process

Processes disclosed in U.S. Patent Application Publication No. 20100029944 and Chinese Patent CN101711248, N,N'-Carbonyldiimidazole (CDI) and N,N'-Carbonyl-di-(1,2,3-tiazole) (CTD) are respectively used for the introduction of carbonyl group of Solifenacin. As CDI and CDT are relatively expensive and in high molecular weights, these processes are not practicably useful for industrial manufacture with high cost and low atom economy. According another process disclosed in Monatsh, Chem. (2011) 142:1181-1186, and WO2010103529, bis(p-nitrophenyl) carbonates (NPC) is used for the introduction of carbonyl group. However, NPC is not favorable to industrial application as it is irritant and harmful.

SUMMARY OF THE INVENTION

The present invention provides an improved method that overcomes the drawbacks of previous technology. The present invention provides a method for preparing the Solifenacin intermediate that is environmentally safe, cost-effective, easy to carry out, and gives high yield.

The present invention provides a process for preparing (1s)-1-phenyl-3,4-dihydro-2(1H)-isoquinoline-carboxylate (Formula I), comprising reacting (1S)-1-phenyl-3,4-dihydro-2(1H)isoquinoline (Formula II) with carbon dioxide and an alkylating agent R-LG in presence of a base to obtain Formula I in an organic solvent as follow.

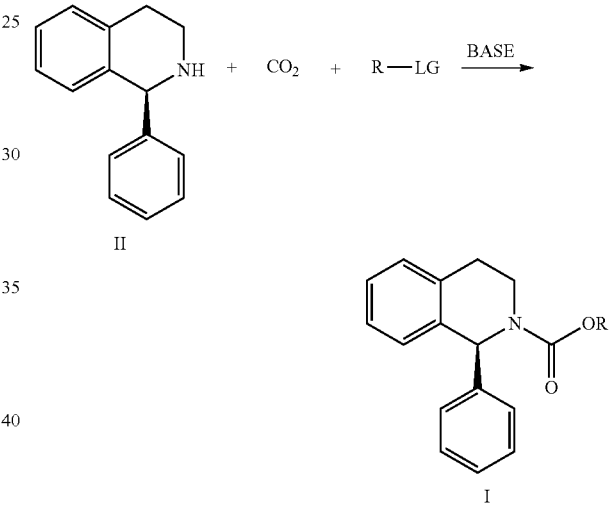

Wherein
R is an alkyl or a substituted alkyl; preferably, a C1-C4 alkyl; and more preferably, a methyl, ethyl, or propyl;
LG is a leaving group, preferably a chloro-, bromo-, or Iodo-leaving group;
the pressure of carbon dioxide is equal to or less than 1.0 Mpa;
the base is an inorganic carboxylate or 1,8-Diazabicyclo [5.4.0]undec-7-ene (DBU), or a mixture thereof; when the base is the inorganic carboxylate, it is lithium carbonate, sodium carbonate, potassium carbonate, cesium carbonate, or a mixture thereof;
the ratio of the base to the compound of formula II is (1.0-10.0):1, more preferably 2.0-7.0:1;
the organic solvent is an aprotic polar solvent, preferably, N,N dimethyl formamide, acetonitrile, tetrahedronfuran, dioxane, or a mixture thereof;
the reaction temperature is 0-50° C., preferably 15-30° C.;
the reaction time is 1-10 hours, preferably 1-5 hours.

According to the present invention, at a specific temperature, gaseous carbon dioxide is introduced to keep the required pressure. Alternatively, solid carbon dioxide (dry ice) is added.

The method has been creatively designed and successfully carried out. The present invention solves the problems with the inevitably hazardous chemicals such as triphosgene and chloroformates in the preparation of Solifenacin in the field when synthesizing the intermediate (formula I) with dimethyl carbonate (DMC). The intermediate (formula I) is obtained with an alternative greener, cheaper reagent, i.e., carbon dioxide, such that the process does not have to work well only at an elevated temperature and in a period of long reaction time. Compound of formula II is transformed to the carbonate in organic solvents by introducing gaseous carbon dioxide or dry ice in the presence of the base quickly and under mild condition with a yield up to 100%. Particularly, the carbonate generated from compound of formula II and carbon dioxide are well soluble in organic solvents and active in the subsequent alkylation, and can transform to the highly pure compound of formula I at relatively low temperature with high yield. Compound of formula I maybe subsequently used to prepare Solifenacin by ester transformation without further purification.

The present invention provides a process that is environmentally friendly, cost effective, easy to carry out, with high yield, easy to control impurities, and catalyst-free. The process of the present invention is particularly favorable to industrial production.

DETAILED DESCRIPTION OF THE INVENTION

The present invention is described in details with reference to the following examples, which are provided by the way of illustration only and should not be construed as to limit the scope of the present invention in any manner.

The high pressure reactions in the examples are carry out in a 500 mL stainless steel reactor. In the process of the present invention, at a specific temperature, the gaseous carbon dioxide is introduced into the reactor to keep the needed pressure, alternatively, solid carbon dioxide is used. The gaseous carbon dioxide and dry ice used in the examples are purchased from Shanghai Hong Zhi Industrial Gas Co. Ltd.

EXAMPLE 1

To a stirred solution of (1S)-1-phenyl-3,4-dihydro-2(1H) isoquinoline (1.05 g, 5 mmol) in N,N-dimethylformamide (10 mL), cesium carbonate (10 g, 30 mmol) is added. Then, carbon dioxide is bubbled for 1 hour at the ambient temperature (25° C.). N-propyl bromide (2 g, 16.3 mmol) is added, then, carbon dioxide is introduced for 4.0 hours while maintaining the inner pressure at 0.1 MPa. The reaction mixture is filtered, the solution is collected and evaporated under reduced pressure. Ethyl acetate (30 mL) is added to the residue, the organic phase is washed with water (15 ml) and separated. The organic layer is dried over anhydrous sodium sulfate, filtered, and concentrated to afford crude propyl (1s)-1-phenyl-3,4-dihydro-2(1H)-isoquinoline-carboxylate, 1.4 g, 93.4%, with the following characteristics: HPLC: 98.4%; Chiral Purity: 99%; MS (ESI): m/z 296.2 (M+H$^+$), 318.2 (M+Na$^+$); $^1$-H-NMR (400 M, CDCl3): δ 7.33-7.07 (m, 9H), 6.47 (brs, 1H), 4.16-4.07 (m, 3H), 3.32-3.27 (m, 1H), 3.01 (m, 1H), 2.82-2.76 (m, 1H), 1.72-1.71 (m, 2H), 0.99 (t, 3H).

EXAMPLE 2

To a stirred solution of (1S)-1-phenyl-3,4-dihydro-2(1H) isoquinoline (1.05 g, 5 mmol) in acetonitrile (10 mL), potassium carbonate (5.5 g, 40 ml mmol) is added, then, carbon dioxide is bubbled for 1 hour at 40° C. N-propyl bromide (2 g, 16.3 mmol) is added, then, carbon dioxide is introduced for 5.0 hours while maintaining the inner pressure at 1.0 MPa. The reaction mixture is filtered, the solution is collected and evaporated under reduced pressure. Ethyl acetate (30 mL) is added to the residue, the organic phase is washed with water (15 ml) and separated. The organic layer is dried over anhydrous sodium sulfate, filtered, and concentrated to afford crude propyl (1s)-1-phenyl-3,4-dihydro-2(1H)-isoquinoline-carboxylate, 1.28 g, 96.9%, with the characteristic of HPLC: 88.7%.

EXAMPLE 3

To a stirred solution of (1S)-1-phenyl-3,4-dihydro-2(1H) isoquinoline (1.05 g, 5 mmol) in N,N-dimethylformide (10 mL), sodium carbonate (3.2 g, 30 ml mmol) is added, then carbon dioxide is bubbled for 1 hour at 50° C. Ethyl bromide (2 g, 16.3 mmol) is added, then carbon dioxide is introduced for 9.0 hours while kept the inner pressure at 0.5 MPa. The reaction mixture is filtered, the solution is collected and evaporated under reduced pressure. Ethyl acetate (30 ml) is added to the residue, the organic phase is washed with water (15 ml) and separated. The organic layer is dried over anhydrous sodium sulfate, filtered, and concentrated to afford crude ethyl (1s)-1-phenyl-3,4-dihydro-2(1H)-isoquinoline-carboxylate, 1.0 g, 70.0%, with the following characteristics: HPLC: 97.2%; Chiral Purity: 99%; MS (ESI): m/z 282.2 (M+H$^+$), 304.1 (M+Na$^+$); $^1$-H-NMR (400M, CDCl3): δ 7.33-7.07 (m, 9H), 6.47 (brs, 1H), 4.25-4.14 (m, 3H), 4.14-4.06 (br, 1H), 3.31-3.24 (m, 1H), 3.02 (m, 1H), 1.33-1.29 (t, 3H)

EXAMPLE 4

To a solution of (1S)-1-phenyl-3,4-dihydro-2(1H)isoquinoline (1.05 g, 5 mmol) in N,N-dimethylformamide (10 ml), cesium carbonate (16.3 g, 50 mmol) is added, carbon dioxide is bubbled for 1 hour at 30° C. Methyl Iodide (2.8 g, 20 mmol) is added, then carbon dioxide is introduced for 2.0 hours while maintaining the inner pressure at 0.2 MPa. The reaction mixture is filtered, the solution is collected and evaporated under reduced pressure. Ethyl acetate (30 mL) is added to the residue, the organic phase is washed with water (15 ml) and separated. The organic layer is dried over anhydrous sodium sulfate, filtered, and concentrated to afford crude propyl (1s)-1-phenyl-3,4-dihydro-2(1H)-isoquinoline-carboxylate, 1.12 g, 82.2%, with the following characteristics: HPLC: 98.4%; Chiral Purity: 99%; MS (ESI): m/z 268.2 (M+H$^+$), 291.2 (M+Na$^+$); $^1$-H-NMR (400M, CDCl3): δ 7.33-7.07 (m, 9H), 6.47 (brs, 1H), 4.16-4.06 (br, 1H), 3.79 (s, 1H), 3.01 (m, 1H), 2.82-2.76 (m, 1H).

EXAMPLE 5

To a stirred solution of (1S)-1-phenyl-3,4-dihydro-2(1H) isoquinoline (1.05 g, 5 mmol) in acetonitrile (10 mL), lithium carbonate (1.48 g, 20 mmmol) is added, carbon dioxide is bubbled for 1 hour at 20° C. Methyl iodide (1.4 g, 10 mmol) is added, then carbon dioxide is introduced for 7.0 hours at 50° C. while maintaining the pressure at 0.2 MPa. The reaction mixture is filtered, the solution is collected and evaporated under reduced pressure. Ethyl acetate (30 ml) is added to the residue, the organic phase is washed with water (15 ml) and separated. The organic layer is dried over anhydrous sodium sulfate, filtered, and concentrated to afford crude methyl (1s)-1-phenyl-3,4-dihydro-2(1H)-isoquinoline-carboxylate, 1.09 g, 81.6%.

EXAMPLE 6

To a stirred solution of (1S)-1-phenyl-3,4-dihydro-2(1H) isoquinoline (1.05 g, 5 mmol) in n,n-dimethylformide (10 mL), potassium carbonate (1.38 g, 10 mmmol) is added, then carbon dioxide is bubbled for 1 hour at 25° C. N-propyl bromide (0.6 g, 5 mmol) is added, then carbon dioxide is introduced for 4.0 hours at 50° C. while maintaining the pressure at 0.1 MPa. The reaction mixture is filtered, the solution is collected and evaporated under reduced pressure. Ethyl acetate (30 ml) is added to the residue, the organic phase is washed with water (15 ml) and separated. The organic layer is dried over anhydrous sodium sulfate, filtered, and concentrated to afford crude propyl (1s)-1-phenyl-3,4-dihydro-2 (1H)-isoquinoline-carboxylate, 1.18 g, 80.2%.

EXAMPLE 7

To a stirred solution of (1S)-1-phenyl-3,4-dihydro-2(1H) isoquinoline (1.05 g, 5 mmol) in tetrahedron furan (10 mL), sodium carbonate (2.65 g, 25 mmmol) is added, then carbon dioxide is bubbled for 1 hour at 15° C. N-Butyl bromide (2.01 g, 15 mmol) is added, then carbon dioxide is introduced for 5.0 hours while maintaining the pressure at 0.1 MPa. The reaction mixture is filtered, the solution is collected and evaporated under reduced pressure. Ethyl acetate (30 ml) is added to the residue, the organic phase is washed with water (15 ml) and separated. The organic layer is dried over anhydrous sodium sulfate, filtered, and concentrated to afford crude butyl (1s)-1-phenyl-3,4-dihydro-2(1H)-isoquinoline-carboxylate, 1.30 g, 82.6% with the following characteristics: HPLC: 98.0%; Chiral Purity: 99%; MS (ESI): m/z 310.1 (M+H$^+$), 332.2 (M+Na$^+$); $^1$-H-NMR (400 M, CDCl3): δ 7.33-7.07 (m, 9H), 6.47 (brs, 1H), 4.15-4.07 (m, 3H), 3.32-3.26 (br, 1H), 3.01 (m, 1H), 2.81-2.78 (m, 1H), 1.73-1.63 (m, 4H), 0.96 (t, 3H).

EXAMPLE 8

To a solution of (1S)-1-phenyl-3,4-dihydro-2(1H)isoquinoline (1.05 g, 5 mmol) in dioxane (10 ml), sodium carbonate (2.65 g, 25 mmol) is added, then carbon dioxide is bubbled for 1 hour at 25° C. Ethyl bromide (1.1 g, 10 mmol) is added, then carbon dioxide is introduced for 4.0 hours while maintaining the pressure at 0.1 MPa. The reaction mixture is filtered, the solution is collected and evaporated under reduced pressure. Ethyl acetate (30 ml) is added to the residue, the organic phase is washed with water (15 ml) and separated. The organic layer is dried over anhydrous sodium sulfate, filtered, and concentrated to afford crude ethyl (1s)-1-phenyl-3,4-dihydro-2(1H)-isoquinoline-carboxylate, 1.17 g, 84%.

EXAMPLE 9

To a stirred solution of (1S)-1-phenyl-3,4-dihydro-2(1H) isoquinoline (1.05 g, 5 mmol) in n,n-dimethylformide (10 ml), 1,8-diazabicyclo(5,4,0) undec-7-ene (DBU) (4.56 g, 30 mmmol) is added, then carbon dioxide is bubbled for 1 hour at 25° C. Propyl bromide (2 g, 16.3 mmol) is added, then carbon dioxide is introduced for 7.0 hours while maintaining the pressure at 0.15 MPa. The reaction mixture is filtered, the solution is collected and evaporated under reduced pressure. Ethyl acetate (30 ml) is added to the residue, the organic phase is washed with HCl (1 N) (15 ml×3), water (15 ml×3), and separated. The organic layer is dried over anhydrous sodium sulfate, filtered, and concentrated to afford crude propyl (1s)-1-phenyl-3,4-dihydro-2(1H)-isoquinoline-carboxylate, 0.7 g, 46.7%.

EXAMPLE 10

To a solution of (1S)-1-phenyl-3,4-dihydro-2(1H)isoquinoline (1.05 g, 5 mmol) in n,n-dimethylformide (10 ml), cesium carbonate (10 g, 30 mmmol) is added, then dry ice is added while maintaining the pressure at 0.1 MPa and stirred for 1 hour at 20° C. Propyl bromide (2 g, 16.3 mmol) is added, stirred for another 1 hour. The reaction mixture is filtered, the solution is collected and evaporated under reduced pressure. Ethyl acetate (30 ml) is added to the residue, the organic phase is washed with HCl (1 N) (15 ml×3), water (15 ml×3), and separated. The organic layer is dried over anhydrous sodium sulfate, filtered, and concentrated to afford crude propyl (1s)-1-phenyl-3,4-dihydro-2(1H)-isoquinoline-carboxylate, 1.38 g, 93.1%.

EXAMPLE 11

Preparation of Solifenacin (R)-quinuclidin-3-ol (0.66 g, 5.2 mmol) and sodium hydride (0.21 g, 0.52 mmol, 60%) are dissolved in anhydrous toluene and stirred for 1 hour at 80° C. A solution of propyl (1s)-1-phenyl-3,4-dihydro-2(1H)-isoquinoline-carboxylate (1.4 g, 4.75 mmol) in toluene (10 ml) is added and refluxed for 18 hours. Isopropyl alcohol is removed from the solution by azeotropic distillation during which toluene is necessarily added. The reaction is cooled to ambient temperature when propyl carboxylate is consumed completely according to TLC analysis. The toluene is washed with water and aq. HCl (1N)(10 ml), the organic phase is separated. Saturated sodium bicarbonate (20 ml) is added to the aqueous phase, then extracted with ethyl acetate (20 ml). The combined organic phase is dried over anhydrous sodium sulfate, filtered, and concentrated to afford yellow oil as crude Solifenacin base, 1.1 g, 63.9% with the following characteristics: HPLC: 95.8%; Chiral Purity: 99%; MS (ESI): m/z 363.2 (M+H$^+$); $^1$-H-NMR (400 M, CDCl3): δ 7.32-7.17 (m, 9H), 6.55-6.17 (m, 1H), 4.20-2.90 (m, 1H), 3.36-2.86 (br, 10H), 2.18-1.47 (m, 5H).

We claim:

1. A process for preparing (1s)-1-phenyl-3,4-dihydro-2 (1H)-isoquinoline-carboxylate, comprising reacting (1S)-1-phenyl-3,4-dihydro-2(1H)isoquinoline (Formula II) with carbon dioxide and an alkylating agent in presence of a base to obtain the compound of Formula I in an organic solvent:

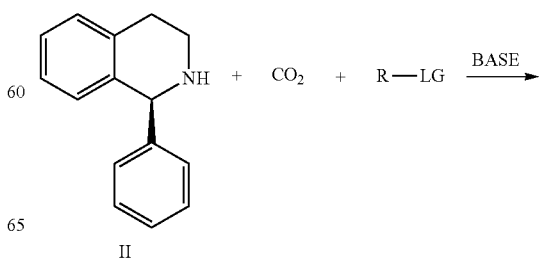

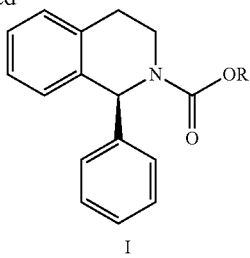

I wherein the alkylating agent is represented by R-LG, R is an alkyl or a substituted alkyl, and LG is a leaving group;

the base is an inorganic carboxylate, 1,8-Diazabicyclo[5.4.0]undec-7-ene (DBU), or a mixture thereof;

the nitrogen on the isoquinoline ring of the compound of formula II reacts and forms the carbamate in the compound of Formula I, and the compound of Formula I is suitable for making pharmaceutical compound.

2. The process according to claim 1, wherein R is a $C_1$-$C_4$ alkyl group.

3. The process according to claim 1, wherein LG is a chloro-, bromo-, or Iodo-leaving group.

4. The process according to claim 1, wherein a ratio of the alkylating agent to the compound of formula II is (1.0-5.0): 1.

5. The process according to claim 1, wherein the carbon dioxide is in gas or solid phase, and a pressure of the carbon dioxide is equal to or less than 1.0Mpa.

6. The process according to claim 1, wherein the base is the inorganic carboxylate.

7. The process according to claim 6, wherein the base is lithium carbonate, sodium carbonate, potassium carbonate, or a mixture thereof.

8. The process according to claim 1, wherein a ratio of the base to the compound of formula II is (1.0-10.0):1.

9. The process according to claim 8 wherein the ratio of the base to the compound of formula II is (2.0-7.0):1.

10. The process according to claim 1, wherein the organic solvent is an aprotic polar solvent.

11. The process according to claim 1, wherein the organic solvent is N,N dimethyl formamide, acetonitrile, tetrahedronfuran, dioxane, or a mixture thereof.

12. The process according to claim 1, wherein reaction temperature is 0-50° C.

13. The process according to claim 12, wherein the reaction temperature is 15-30° C.

14. The process according to claim 1, wherein reaction time is 1-10 hours.

15. The process according to claim 14, wherein the reaction time is 1-5 hours.

16. The process according to claim 1, wherein the base is cesium carbonate or a mixture of cesium carbonate with DBU.

* * * * *